US006498032B1

(12) United States Patent
Clements et al.

(10) Patent No.: US 6,498,032 B1
(45) Date of Patent: Dec. 24, 2002

(54) USE OF CERAMIC LABELS FOR IDENTIFYING BIOMOLECULE IMMOBILIZING SUBTRATES

(75) Inventors: James G. Clements, Brentwood, NH (US); Gregory R. Martin, Acton, ME (US); Kimberly A. Moore, Corning, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 09/475,774

(22) Filed: Dec. 30, 1999

Related U.S. Application Data

(60) Provisional application No. 60/148,262, filed on Aug. 11, 1999.

(51) Int. Cl.[7] .............................. C12M 1/34; C12Q 1/68; C12P 19/34; C07H 21/02; C07H 21/04
(52) U.S. Cl. .................. 435/287.2; 435/6; 435/91.1; 435/287.1; 435/288.4; 536/23.1; 536/24.3
(58) Field of Search ........................ 435/6, 91.1, 183, 435/283.1, 287.1, 287.2, 288.4, 288.7; 436/94; 536/23.1, 24.33, 25.3, 24.3; 422/50, 68.1

(56) References Cited

U.S. PATENT DOCUMENTS

| 5,111,344 A | * | 5/1992 | Ribinson, Jr. ............... 359/900 |
| 5,362,554 A | | 11/1994 | Holzer ........................ 428/283 |
| 5,683,786 A | * | 11/1997 | Kavanaugh ................. 428/195 |
| 5,807,522 A | * | 9/1998 | Brown et al. ................. 422/50 |
| 5,919,553 A | | 7/1999 | Kavanaugh ................. 428/195 |
| 6,043,038 A | * | 3/2000 | Sivaraja et al. ................ 435/6 |
| 6,165,594 A | * | 3/2000 | Moh et al. .................. 428/207 |

FOREIGN PATENT DOCUMENTS

WO          99/36901       7/1999 ............. G09F/3/02

* cited by examiner

*Primary Examiner*—Ethan C. Whisenant
*Assistant Examiner*—Frank Lu
(74) *Attorney, Agent, or Firm*—Thomas R. Beall; Scott S. Serville

(57) ABSTRACT

This invention provides a labeling format for use in assays that require the immobilization of biomolecules on a flat substrate surface. The ceramic labeling indicia of the present invention provide a format that can supply the user with required identification about the substrate and its content without adversely affecting a chemically active surface required for probe immobilization.

6 Claims, 1 Drawing Sheet

USE OF CERAMIC LABELS FOR IDENTIFYING BIOMOLECULE IMMOBILIZING SUBTRATES

This application claims the benefit of U.S. provisional patent application Ser. No. 60/148,262 filed on Aug. 11, 1999 entitled USE OF CERAMIC LABELS FOR IDENTIFYING BIOMOLECULE IMMOBILIZING SUBSTRATES by James G. Clements, Gregory R. Martin, and Kimberly A. Moore.

FIELD OF THE INVENTION

The present invention relates generally to the field of laboratory test slides, and specifically to the use of patterned ceramic indicia as a labeling means for substrates used to immobilize biomolecules.

BACKGROUND OF THE INVENTION

High density arrays are new tools used by drug researchers and geneticists which provide information on the expression of genes from particular cells. A high density array typically comprises between 5,000 and 50,000 probes in the form of DNA strands, each of known and different sequence, arranged in a determined pattern on a substrate. The substrate may be any size but typically takes the form of a 1×3 inch glass microscope slide.

The arrays are used to determine whether target sequences interact or hybridize with any of the probes on the array. After exposing the array to target sequences under selected test conditions, scanning devices can examine each location in the array and determine whether a target molecule has hybridized with the probe at that location. DNA arrays can be used to study which genes are "turned on" or up-regulated and which genes are "turned off" or down-regulated. So for example, a researcher can compare a normal colon cell with a malignant colon cell and thereby determine which genes are being expressed or not expressed only in the aberrant cell. The regulation of these genes serves as key targets for drug therapy.

In order to immobilize the probe sequence to the substrate, a coating is applied to the slide to enhance the attachment. One common film that is applied for this purpose is gamma aminopropyltriethoxylsilane (GAPS). After such a coating is applied, the DNA is printed onto the substrate surface by any number of printing methods including piezoelectric, typo pin printing, capillary pin printing, ink jet printing, etc. The end result is an array with spots of immobilized probes at a pitch of between 10–500 $\mu$m.

A means for linking the physical slide and the vast amount of genetic information contained on it, to a corresponding database which stores information about each of the thousands of sequences contained on the slide, is required. This link takes the form of a bar code label, for example. In order to meet a market demand for pre-coated GAPS slides for use by customers to print their own arrays, the Assignee of the present invention prepared a product for market. Applicants affixed adhesive bar code labels to the surface of the coated slides and stored them at various conditions as a test in preparation for product release.

It was discovered that the GAPS coated slides having the bar-code labels were becoming progressively less effective at immobilizing DNA probes over time, while non-labeled slides remained effective. This discovery led to focused study on the effects of the labeling on the chemistry of the GAPS coating. After some study, it became clear that the chemical adhesive from the bar code label was deleteriously affecting the GAPS surface film. The present invention solves the problem caused with adhesive labels by providing a chemically inert labeling system for substrates designed to immobilize biomolecules.

SUMMARY OF THE INVENTION

This invention provides a labeling format for use in assays that require the immobilization of biomolecules on a flat substrate surface. The ceramic labeling indicia of the present invention provide a format that can supply the user with required identification about the substrate and its content without adversely affecting a chemically active surface required for probe immobilization.

DETAILED DESCRIPTION OF THE INVENTION

Figure 1:
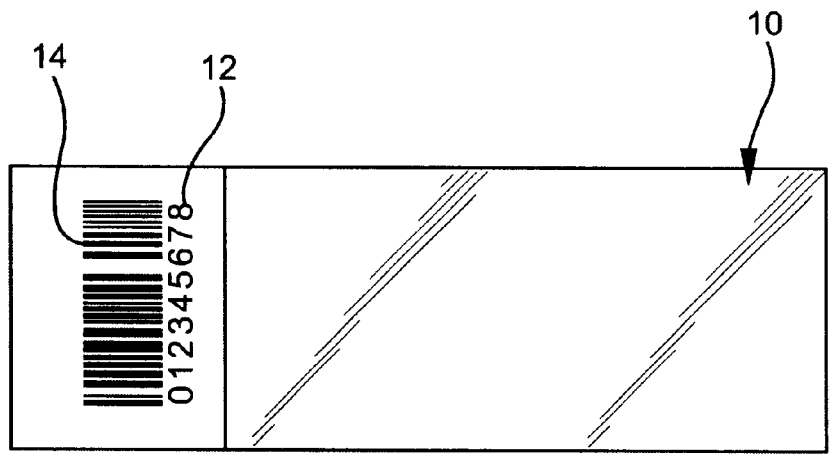
FIG. 1 is a plan view of the substrate of the present invention.

In FIG. 1, a substrate 10 having alphanumeric ceramic labeling 12 and bar-code ceramic labeling 14 is shown. The substrate may be any shape and dimension, but preferably conforms to the dimensions of a standard microscope slide. The substrate 10 may be made from a variety of materials including, but not limited to: soda lime glass, borosilicate glass, ceramic, or metals such as nickel, titanium, or aluminum. Glass substrates, in the form of alkaline metal borosilicate, borosilicate, or soda lime glass are preferred.

The labeling 10, 12, whether bar code, lettering, numbering or other indicia is an opaque ceramic material having a firing temperature compatible with the annealing temperature of the glass substrate (greater than 500° C.). A listing of acceptable ceramic formulations can be found in U.S. Pat. No. 5,111,344, incorporated herein by reference. The frit may contain both ceramic and glass particles (or a mixture of the two) and can either be used alone or with coloring agents. With the addition of a conventional carrier oil such as pine oil, the formulations produce an excellent ceramic frit that, when screened through a mask, may either be applied to a substrate or to an adhesive sheet material which itself may be applied to a substrate surface. Ceramic labels consisting of a frit indicia printed on an adhesive tape are commercially available from 3M, and Ceralabel products (through Silver Creek Associates, Houston Tex.). Descriptive methodologies for producing such labels are described fully in WO 99/36901 and U.S. Pat. No. 5,362,554, for example.

The process for making a ceramic labeled substrate for the immobilization of biomolecules follows:

1) A commercially available ceramic label is obtained. The label contains indicia screen printed onto a release paper backing. The indicia will enable identification and tracking of the substrate. The indicia are attached to the paper by an adhesive.

2) A commercially available soda-lime glass microscope slide (Erie Scientific) is prepared by conventional washing and drying. Any conventional drying method and means may be used, e.g., strip heaters or hot air blowers. This step should take about one minute in a 200° C. oven. The result is a microscope slide free of extraneous material.

3) The ceramic label is affixed to one end of the microscope slide by transfer and removal from the paper backing.

The slide is then fired in order to both burn off the adhesive attached to the ceramic frit as well as to fuse the ceramic label to the glass slide. In this step, the ceramic-labeled slides are heated to a temperature and for a time that would soften the surface of the glass slides and fire the ceramic coating to the point that the coating will fuse into the softened glass and produce a porous, matte ceramic surface. Specifically, the ceramic-coated glass slides are heated in an oven where the ceramic is fired at a temperature below the effective annealing temperature of the soda-lime glass (approximately 500° C.). Depending on the color additives, if any, the ceramic firing temperature should range from approximately 470° C. to approximately 495° C. for a long soak time of approximately 12–15 minutes. This oven temperature should be maintained at a uniform level plus or minus 5 degrees C. At these temperatures and time ranges, the glass surface softens to the extent necessary to enable the fired ceramic coating to fuse into the glass without distorting it. Alternatively, the firing temperature of the ceramic may exceed the effective annealing temperature of the glass provided the soak time is reduced to the point that the glass surface softens to the extent necessary to enable the fired ceramic coating to fuse into the glass without distorting it. This alternative is based on common knowledge—that temperature and time ranges are usually inversely related, that is, higher temperatures require shorter heating times and lower temperatures require longer heating times. Naturally, for alternate glasses, adjustments to the temperature should be made based on the relative annealing temperature of the glass.

5) The next step is the cooling of the ceramic-fused glass slides, e.g., about forty-five minutes of slow gradual cooling in a dust and contamination free environment.

6) After the substrate is labeled and cooled, the immobilization chemistry coating may be applied. In a preferred embodiment, GAPS is applied according to any variety of methods including dip coating and CVD coating. Other biologically active surface coatings that may be applied include: any organosilane, streptavidin, or poly-d-lysine, as examples.

Figure 2:
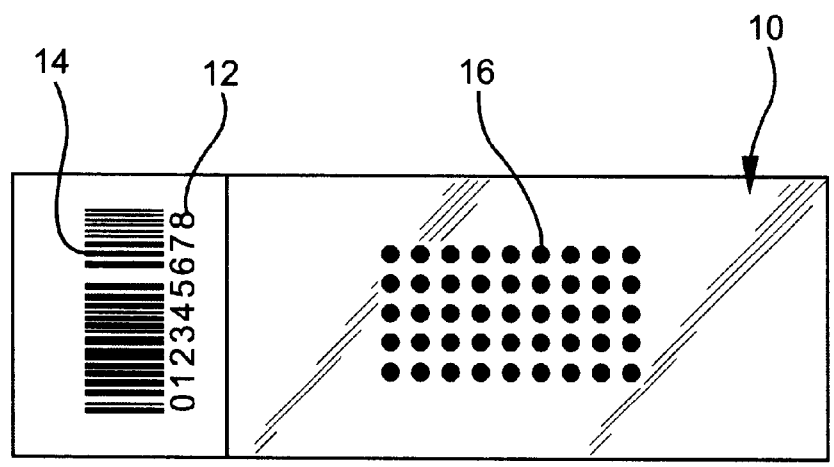
FIG. 2 is a plan view of the substrate of the present invention having an array of biomolecules attached thereto.

After the proper coating is applied, the substrate is properly prepared for accepting biomolecules. FIG. 2 shows the substrate 10 after an array 16 of biomolecules, preferably nucleic acid probes, has been deposited. The on-center spacing of the biomolecules as between adjacent row and adjacent columns, is preferably between 50–500 $\mu$m. Biomolecules that may be immobilized on the substrate include: specific binding members (e.g., antigens, ligands, and haptens), proteins, (e.g., binding proteins, receptor proteins, antibodies, and antibody fragments), nucleic acids (e.g., RNA and DNA molecules), and the like, or even full cells.

In a preferred embodiment, an array of nucleic acid probes is deposited on the substrate by any of the means previously described, i.e. mechanical deposition as described in U.S. Pat. No. 5,807,522, piezoelectric deposition as described in U.S. Pat. No. 5,474,796, or massively parallel typo-pin printing as described in WO9955460, etc.

Although the invention has been described in detail for the purpose of illustration, it is understood that such detail is solely for that purpose and variations can be made therein by those skilled in the art without departing from the spirit and scope of the invention which is defined by the following claims.

What is claimed is:

1. A substrate comprising:

(a) a substantially flat slide having an upper and lower surface, at least one of the surfaces including a surface chemistry adapted to accept a biomolecule;

(b) a ceramic labeling indicia bonded to either the upper surface or lower surface of said slide, whereby the indicia itself is ceramic and chemically inert to the surface chemistry.

2. The substrate of claim 1 wherein the surface chemistry further includes a biomolecular immobilizing film coating said upper surface of said slide.

3. The substrate of claim 2 further comprising a biomolecule attached to said upper surface of said substrate.

4. The substrate of claim 3 wherein said biomolecule is a DNA probe.

5. The substrate of claim 1 further comprising an array of biomolecules attached to the upper surface of said slide.

6. The substrate of claim 5 wherein said array further comprises a matrix of spotted biomolecule locations whereby said locations are spaced between 10–500 $\mu$m apart.

* * * * *